(12) United States Patent
Atherton

(10) Patent No.: US 10,322,252 B2
(45) Date of Patent: Jun. 18, 2019

(54) ERGONOMIC NASAL CANNULA

(71) Applicant: Darin B Atherton, Meridian, ID (US)

(72) Inventor: Darin B Atherton, Meridian, ID (US)

( * ) Notice: Subject to any disclaimer, the term of this patent is extended or adjusted under 35 U.S.C. 154(b) by 377 days.

(21) Appl. No.: 15/206,759

(22) Filed: Jul. 11, 2016

(65) Prior Publication Data

US 2017/0007794 A1 Jan. 12, 2017

Related U.S. Application Data

(60) Provisional application No. 62/191,091, filed on Jul. 10, 2015.

(51) Int. Cl.
| | | |
|---|---|---|
| *A61M 16/01* | (2006.01) | |
| *A61M 16/06* | (2006.01) | |
| *A61M 16/12* | (2006.01) | |
| *A61M 16/20* | (2006.01) | |

(52) U.S. Cl.
CPC ........ *A61M 16/01* (2013.01); *A61M 16/0666* (2013.01); *A61M 16/0672* (2014.02); *A61M 16/125* (2014.02); *A61M 16/20* (2013.01); *A61M 2205/0205* (2013.01)

(58) Field of Classification Search
CPC .......... A61M 16/0672; A61M 16/0666; A61M 16/20; A61M 16/125; A61M 15/08; A61M 16/208; A61F 5/56
See application file for complete search history.

(56) References Cited

U.S. PATENT DOCUMENTS

| | | | |
|---|---|---|---|
| 8,844,533 B2 * | 9/2014 | Allum | A61M 16/0666 128/205.24 |
| 2003/0106555 A1 * | 6/2003 | Tovey | A61M 15/08 128/205.27 |
| 2010/0059053 A1 * | 3/2010 | Niland | A61L 29/16 128/203.18 |
| 2012/0227742 A1 * | 9/2012 | Witt | A61M 16/0666 128/205.24 |
| 2013/0081637 A1 * | 4/2013 | Foley | A61F 5/08 128/848 |

FOREIGN PATENT DOCUMENTS

EP 2371413 A1 * 10/2011 ........ A61M 16/0666

* cited by examiner

*Primary Examiner* — Jan Christopher L Merene
*Assistant Examiner* — Cana A Gallegos

(57) ABSTRACT

An ergonomic nasal cannula that maximizes comfort, decreases oxygen waste, and reduces nasal pain, bacterial growth, and infections includes a nasal cushion and an airflow structure. The airflow structure supports the nasal cushion and facilitates the flow of oxygen from a nasal cannula tubing to the airway of a user, via the nasal cushion. The nasal cushion is a soft, pliable structure that rests against the nasal cavity of the user, wherein a nasal opening allows for the flow of oxygen into the nasal cavity. An anti-pathogenic material, such as elemental silver, is impregnated into the nasal cushion in order to eliminate harmful pathogens and prevent infections. A two-way valve is integrated into an outer lateral wall of the airflow structure, allowing for the introduction of inspired oxygen and preventing the build-up of pressure.

11 Claims, 16 Drawing Sheets

ERGONOMIC NASAL CANNULA

The current application claims a priority to the U.S. Provisional Patent application Ser. No. 62/191,091 filed on Jul. 10, 2015.

FIELD OF THE INVENTION

The present invention relates generally to nasal cannulas. More specifically, the present invention is a new and innovative nasal cannula that maximizes comfort, reduces nasal pain, bacterial growth, infections and decreases oxygen waste by an estimated 25-30% by enclosing the cannula, preventing the escape of oxygen when worn.

BACKGROUND OF THE INVENTION

Nasal cannulas are used to deliver oxygen from a tank and consist of a lightweight, rigid tube which splits into two prongs that are placed in the nostrils. Nasal cannulas have not changed since they were invented and patented by Wilford Jones in 1949 despite the growing number of oxygen users and observable customer pain points. Throughout various studies it was found that the cannula pain points include bleeding, ulcers, and infections resulting from the nasal cannula prongs that contact the inner nose. Therefore it is the main objective of the present invention to provide an ergonomic nasal cannula that reduces nasal pain, bacterial growth and infections in users when worn. Additionally, it was discovered that the continuous oxygen flow is wasteful and impacts user cost in the long run. Therefore, it is another objective of the present invention to provide a nasal cannula that does not waste oxygen and reduces the long term costs.

The present invention is an ergonomic nasal cannula that, in the preferred embodiment, can be retrofit to any standard oxygen cannula on the market today. A nasal cushion, preferably made of silicone, is both soft and pliable allowing for complete comfort while reducing pressure and maintaining the nostrils natural moisture, thus preventing drying of the nasal membranes. The nasal cushion will be impregnated with an anti-pathogenic material such as elemental silver to eliminate harmful pathogens. This will prevent infections caused by contaminated sores in the nose. Furthermore, the nasal cushion will rest against the rim of the user's nose, creating a seal to conserve oxygen. A two-way valve, integrated into an airflow structure to which the nasal cushion is connected, allows for the buildup of pressure to be released, preventing the present invention from being expelled from the nose. Additionally, the two-way valve will allow for the desired fraction of inspired oxygen (FiO2%). In another embodiment of the present invention, the ergonomic nasal cannula will be permanently fixed to the nasal cannula tubing.

DETAIL DESCRIPTIONS OF THE INVENTION

All illustrations of the drawings are for the purpose of describing selected versions of the present invention and are not intended to limit the scope of the present invention.

The present invention is an ergonomic nasal cannula that maximizes comfort, decreases oxygen waste by an estimated 25-30%, and reduces nasal pain, bacterial growth, and infections. In the preferred embodiment, the present invention will be able to retrofit to any standard oxygen cannula on the market. The present invention will fit over the nasal prongs of the existing nasal cannulas, providing a comfortable barrier between the prongs and the user's nose. The present invention will not be inserted into the nasal cavity like the traditional nasal prongs, but will simply rest against the rim of the user's nose. This will reduce irritation that is typically caused by the nasal prongs contacting the inner surface of the user's nose.

Figure 1:
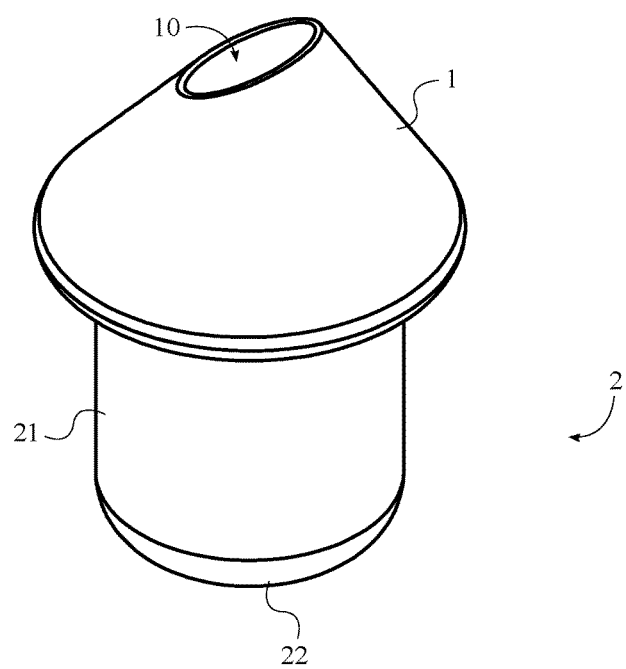
FIG. 1 is a perspective view of the ergonomic nasal cannula.
Figure 2:
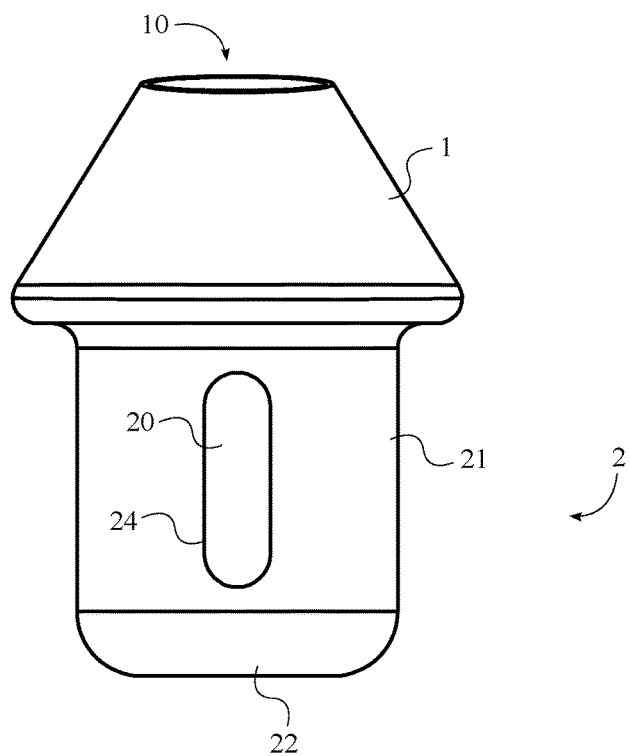
FIG. 2 is a front elevational view of the ergonomic nasal cannula, wherein the secondary airflow opening leads directly to the secondary airflow channel.
Figure 3:
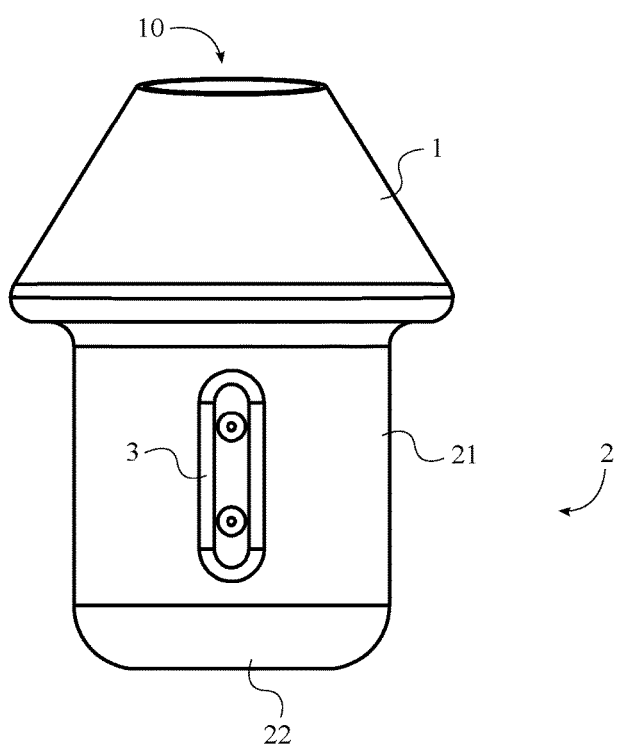
FIG. 3 is a front elevational view of the ergonomic nasal cannula, wherein the two-way valve is mounted to the outer lateral wall, within the secondary airflow opening.

In order to provide optimal comfort and air flow, the ergonomic nasal cannula comprises a nasal cushion 1 and an airflow structure 2 as depicted in FIG. 1. In reference to FIG. 1-3, the nasal cushion 1 is supported by the airflow structure 2, wherein the airflow structure 2 facilitates the flow of oxygen from a nasal cannula tubing 5 to the nasal cushion 1. The nasal cushion 1 is pressed against the nasal cavity of the user, such that oxygen may flow from the nasal cannula tubing 5 into the airway of the user. By resting against the user's nose, the nasal cushion 1 creates a seal which reduces the amount of oxygen wasted. Furthermore, the nasal cushion 1 is tapered away from the airflow structure 2 to match the nasal cavity of the user, increasing the comfort of the nasal cushion 1 and the effectiveness of the seal formed between the nasal cushion 1 and the nasal cavity.

Figure 4:
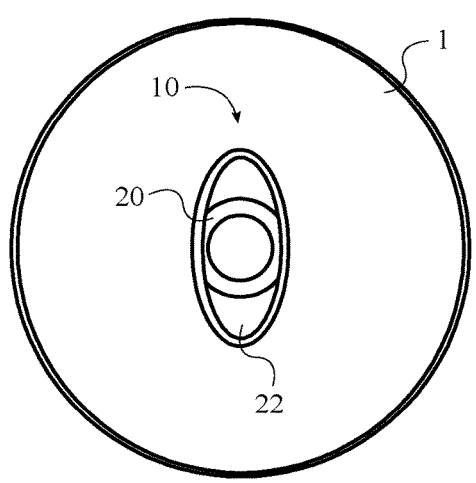
FIG. 4 is a top plan view of the ergonomic nasal cannula, detailing the nasal opening.
Figure 6:
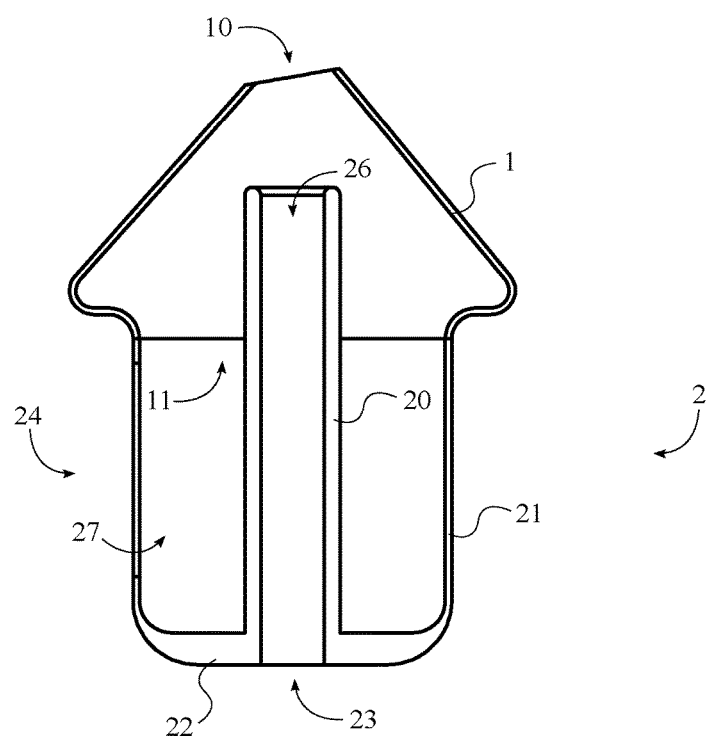
FIG. 6 is a right side sectional view, detailing the secondary airflow opening traversing through the outer lateral wall.
Figure 7:
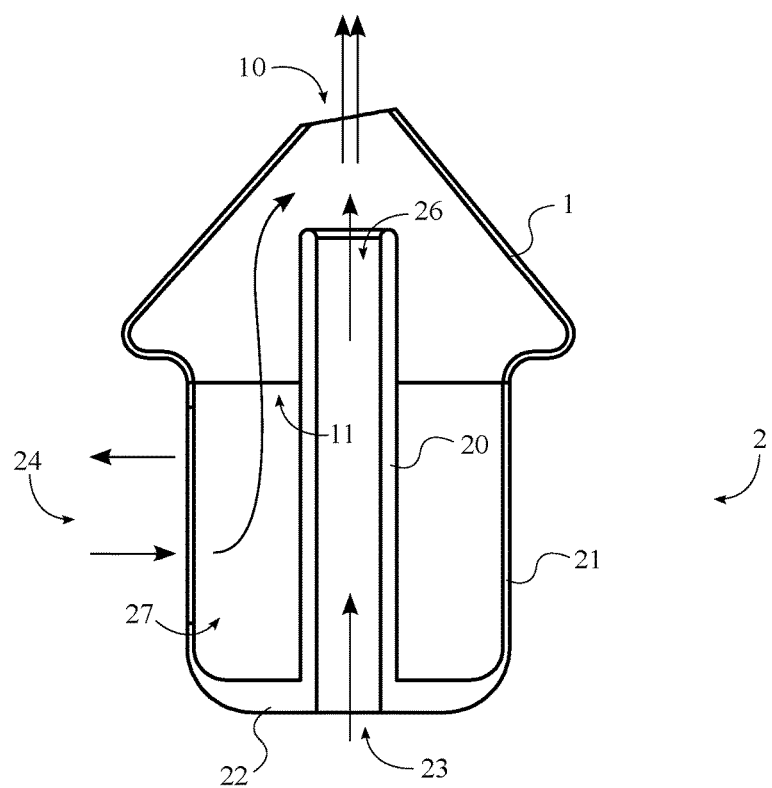
FIG. 7 is a right side sectional view, detailing the flow of oxygen through the secondary airflow opening.

The nasal cushion 1 is a hollow, cone shaped component that is designed to sit against the rim of the user's nose. The nasal cushion 1 is made from a soft and pliable material such as silicone to conform to the opening of the user's nose when properly worn. Furthermore, the nasal cushion 1 is an open ended structure that comprises a nasal opening 10 and a base opening 11 to facilitate the flow of oxygen through the nasal cushion 1, as depicted in FIG. 6-7. The nasal opening 10 is a small, oval shaped cutout arranged at the top of the nasal cushion 1, as depicted in FIG. 4. When worn by the user, the outer surface of the nasal cushion 1 sits against the rim of the user's nose, with the nasal opening 10 positioned up toward the nasal cavity. The wall of the nasal cushion 1 must be thin to flex and conform to the opening of the user's nose.

Figure 16:
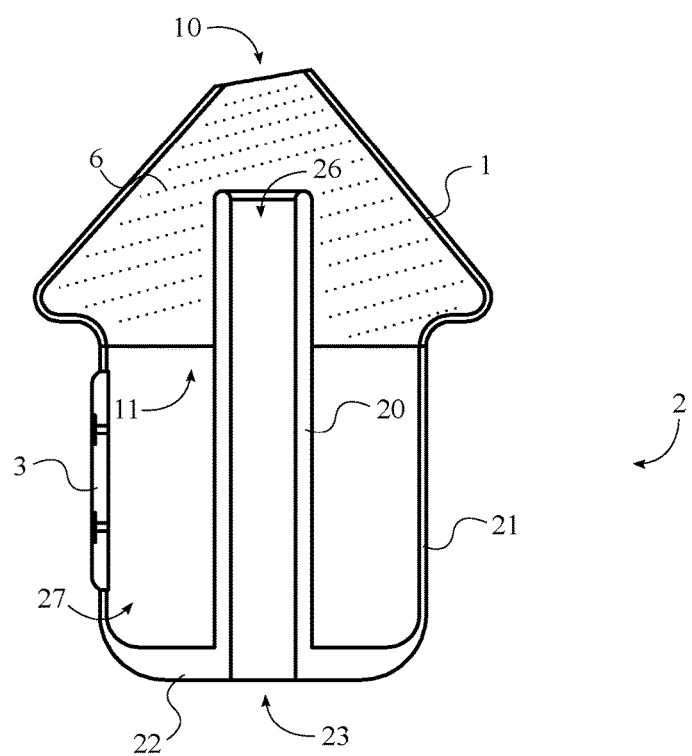
FIG. 16 is a right side sectional view, detailing the anti-pathogenic material impregnated within the nasal cushion.

The prolonged use of typical nasal prongs can lead to abrasions within and around the nasal cavity, which can lead to the introduction of harmful pathogens and in turn infections. While the design of the nasal cushion 1 is intended to reduce pain points, prolonged use may still lead to some degree of irritation. In reference to FIG. 16, in order to prevent the introduction of harmful pathogens that may cause infections in the nose, the nasal cushion 1 is impregnated with an anti-pathogenic material 6 to eliminate said pathogens. In the preferred embodiment of the present invention, the nasal cushion 1 is constructed from a silicon material and is impregnated with the anti-pathogenic material 6 being elemental silver, which has been scientifically proven to eliminate harmful pathogens. Other embodiments may include various material combinations of the nasal cushion 1 and the anti-pathogenic material 6 to enhance the comfort of the user, while preventing infections.

The airflow structure 2 supports the nasal cushion 1 and facilitates the flow of oxygen from the nasal tubing to the user's airway via the nasal cushion 1. In reference to FIG. 6-11, the airflow structure 2 comprises an inner lateral wall 20, an outer lateral wall 21, a base plate 22, a primary airflow opening 23, and a secondary airflow opening 24. The inner lateral wall 20, the outer lateral wall 21, and the base plate 22 form the support structure to which the nasal cushion 1 is mounted and define a primary airflow channel 26 and a secondary airflow channel 27 that are utilized to deliver oxygen to the user. Meanwhile, the primary airflow opening 23 and the secondary airflow opening 24 facilitate the flow of oxygen into the primary airflow channel 26 and the secondary airflow channel 27 respectively.

In further reference to FIG. 6-11, the inner lateral wall 20 and the outer lateral wall 21 are terminally connected to the base plate 22; the inner lateral wall 20 and the outer lateral wall 21 being connected to the same side of the base plate 22. Each of the inner lateral wall 20 and the outer lateral wall 21 is a thin-walled structure that extends away from the base plate 22. The inner lateral wall 20 is perimetrically positioned around the primary airflow opening 23, wherein the primary airflow opening 23 traverses through the base plate 22. Both the inner lateral wall 20 and the primary airflow opening 23 delineate the primary airflow channel 26; the inner lateral wall 20 forming a tube structure extending away from the base plate 22. The primary airflow opening 23 is in fluid communication with the primary airflow channel 26, to facilitate the flow of oxygen from the nasal tubing to the user's airway, through the airflow structure 2.

The outer lateral wall 21 is perimetrically positioned around the base plate 22, wherein the inner lateral wall 20 is positioned within the outer lateral wall 21. Together, the outer lateral wall 21 and the inner lateral wall 20 delineate the secondary airflow channel 27; the secondary airflow channel 27 being the hollow space formed between the inner lateral wall 20 and the outer lateral wall 21. In reference to FIG. 6-7, the secondary airflow opening 24 traverses through the outer lateral wall 21, wherein the secondary airflow channel 27 is in fluid communication with the secondary airflow opening 24. The secondary airflow opening 24 serves to introduce inspired oxygen from the surrounding environment that is mixed with the pure oxygen supplied by the nasal tubing. Furthermore, the secondary airflow opening 24 allows air to be expelled from the airflow structure 2, preventing pressure buildup and allowing the user to exhale. The ability for a buildup of pressure to be released, prevents the nasal cushion 1 from being expelled from the nose during unexpected occurrences or pressure buildups, such as sneezing.

Figure 8:
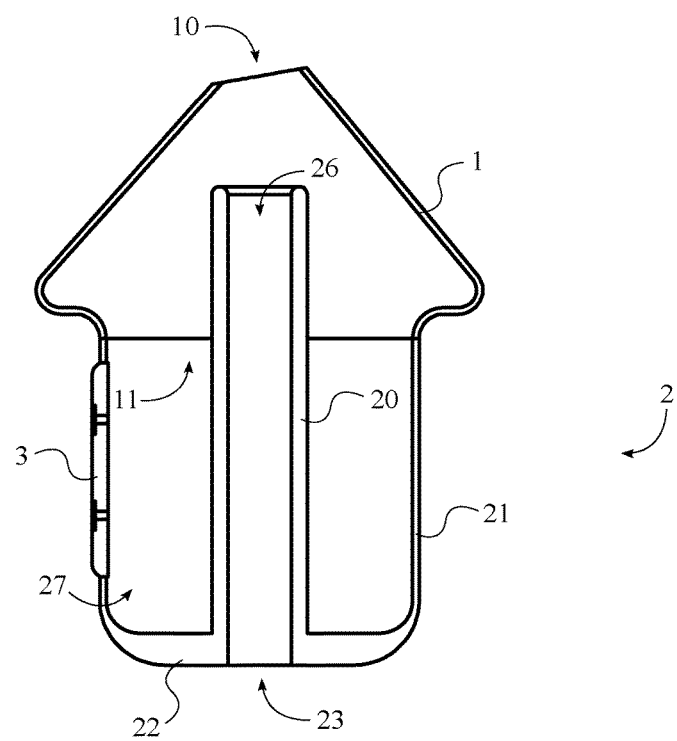
FIG. 8 is a right side sectional view, detailing the two-way valve being mounted into the outer lateral wall.
Figure 9:
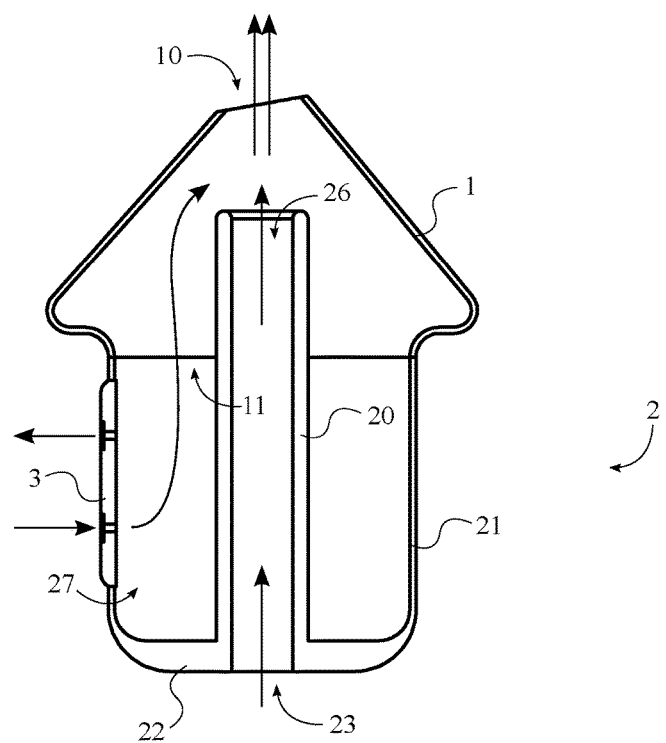
FIG. 9 is a right side sectional view, detailing the flow of oxygen through the two-way valve.
Figure 10:
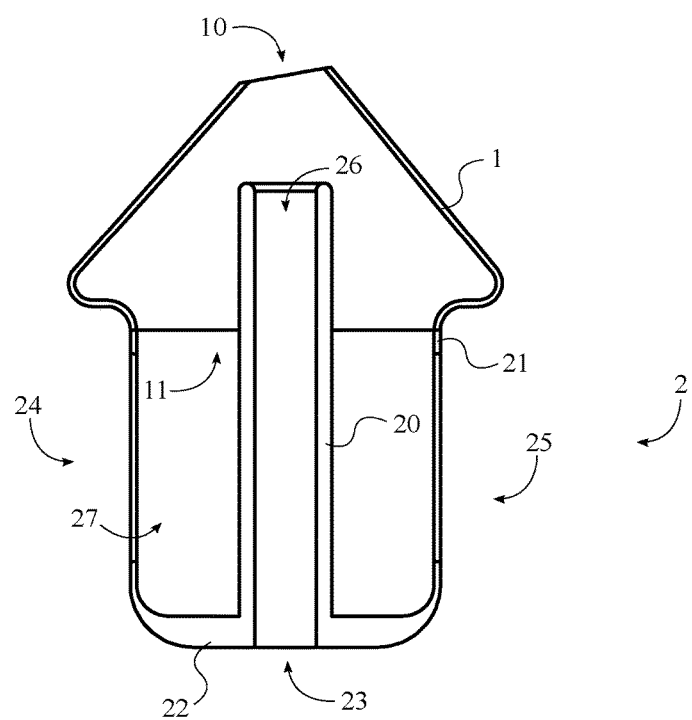
FIG. 10 is a right side sectional view, wherein the airflow structure comprises a tertiary airflow opening.
Figure 11:
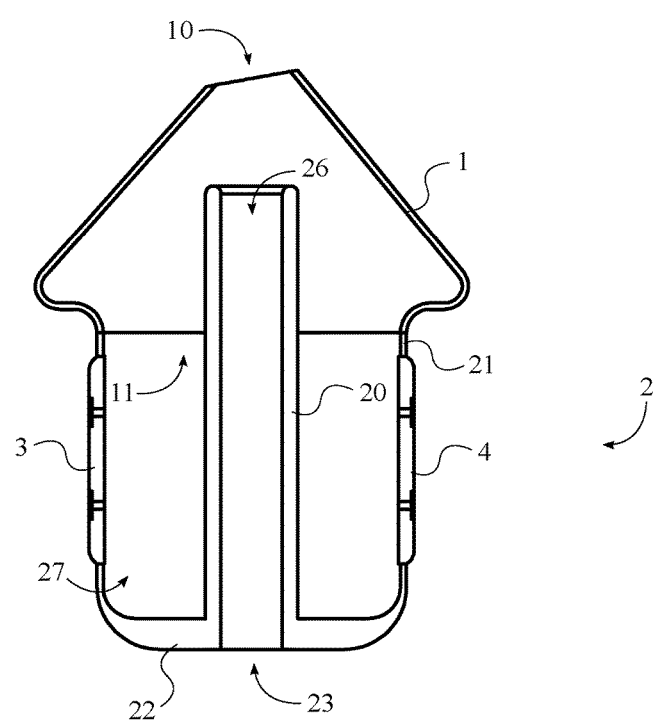
FIG. 11 is a right side sectional view, wherein a subsequent two-way valve is mounted to the outer lateral wall, within the tertiary airflow opening.

In reference to FIG. 8-9, the present invention may further comprise a two-way valve 3 that is used to control the influx of inspired oxygen and the efflux of air exhaled by the user. The two-way valve 3 is positioned within the secondary airflow opening 24, wherein the two-way valve 3 is mounted to the outer lateral wall 21. The two-way valve 3 being integrated into the airflow structure 2 allows for the more controlled influx and efflux of air. For example, the two-way valve 3 can be configured such that the force required to inhale air is less than the force required to exhale air, or vice versa. The inspired oxygen pulled into the secondary airflow channel 27 through the two-way valve 3 mixes with the pure oxygen being pumped in via the primary airflow channel 26, prior to entering the user's nostrils. By changing the force required to inhale air through the two-way valve 3, the desired ratio of inspired oxygen to pure oxygen can be achieved.

It may be necessary to add additional openings or two-way valves in the outer lateral wall 21 to allow for more "on demand" air flow, as the secondary airflow opening 24 or the two-way valve 3 alone may not be sufficient in providing the desired flow of air into and out of the secondary airflow channel 27. In reference to FIG. 10, in one embodiment, the airflow structure 2 further comprises a tertiary airflow opening 25, wherein the tertiary airflow opening 25 traverses through the outer lateral wall 21. The tertiary airflow opening 25 allows for the flow of air into and out of the secondary airflow channel 27 at two locations, thus increasing the flow rate into and out of the secondary airflow channel 27. In reference to FIG. 11, a subsequent two-way valve 4 can also be utilized, wherein the subsequent two-way valve 4 is positioned within the tertiary airflow opening 25 and mounted to the outer lateral wall 21. More or less openings and valves may be utilized in other embodiments of the present invention, depending on the desired flow rate and ease of inhaling and exhaling through the secondary airflow channel 27.

The nasal cushion 1 is perimetrically connected to the outer lateral wall 21 opposite the base plate 22, wherein the base opening 11 is positioned adjacent to the outer lateral wall 21, as depicted in FIG. 6. As such, the nasal opening 10 is terminally positioned opposite the base opening 11. The inner lateral wall 20 traverses into the nasal cushion 1 through the base opening 11, such that the primary airflow channel 26 extends into the nasal cushion 1. In the preferred embodiment of the present invention, the inner lateral wall 20 extends approximately two thirds of the combined length of the airflow structure 2 and the nasal cushion 1, ensuring the pure oxygen is directed to the nasal opening 10, while maintaining enough space within the nasal cushion 1 to allow for the introduction of the inspired oxygen.

Figure 5:
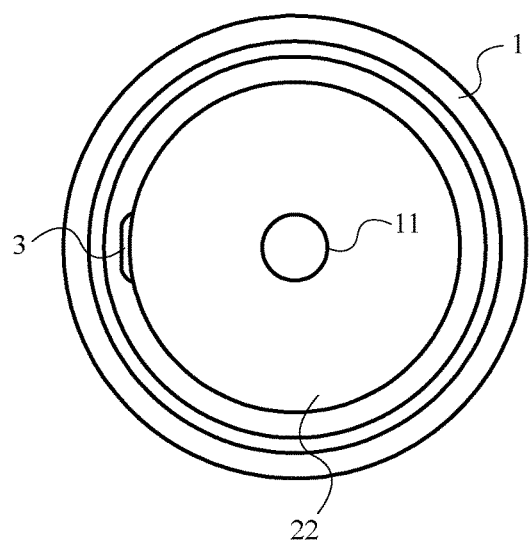
FIG. 5 is a bottom plan view of the ergonomic nasal cannula, detailing the primary airflow opening.

In reference to FIG. 7 and FIG. 9, the base opening 11 is in fluid communication with the secondary airflow channel 27, such that air may travel through the nasal cushion 1 to the secondary airflow opening 24 and vice versa. In reference to FIG. 5, in the preferred embodiment of the present invention, the primary airflow opening 23 is circular and is concentrically positioned with the base plate 22, such that the inner lateral wall 20 is concentrically positioned with both the base plate 22 and the outer lateral wall 21. Furthermore, the base plate 22 is circular in the preferred embodiment, such that the airflow structure 2 is cylindrical in shape with the primary airflow channel 26 centrally traversing along airflow structure 2 and the secondary airflow channel 27 forming an outer ring around the primary airflow channel 26.

Figure 12:
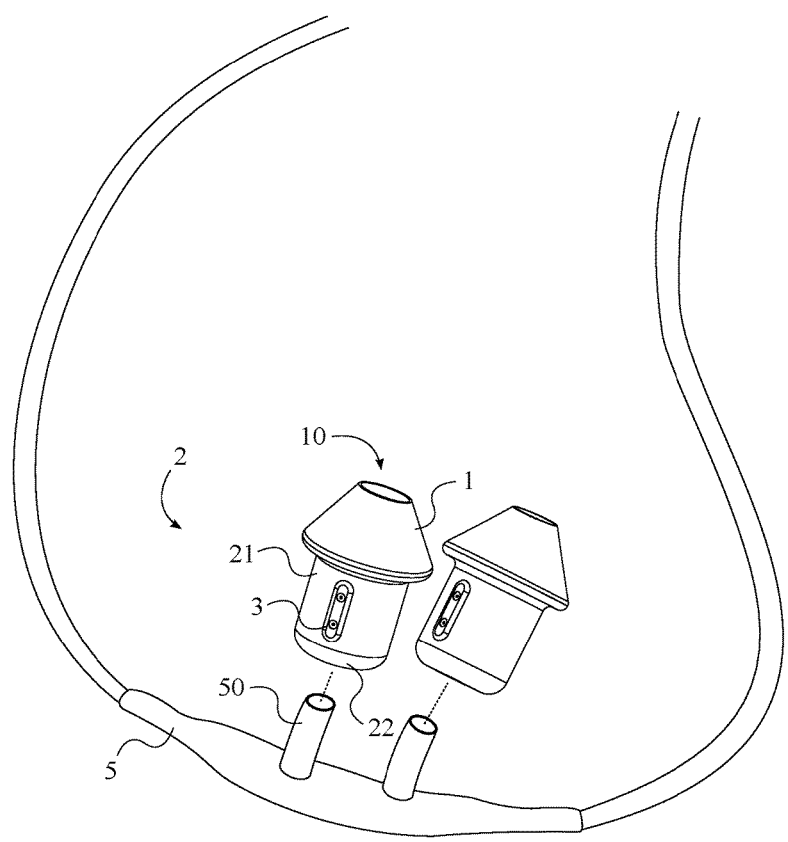
FIG. 12 is a perspective view detailing the alignment of the primary airflow opening and the primary airflow channel with the nasal prong.
Figure 13:
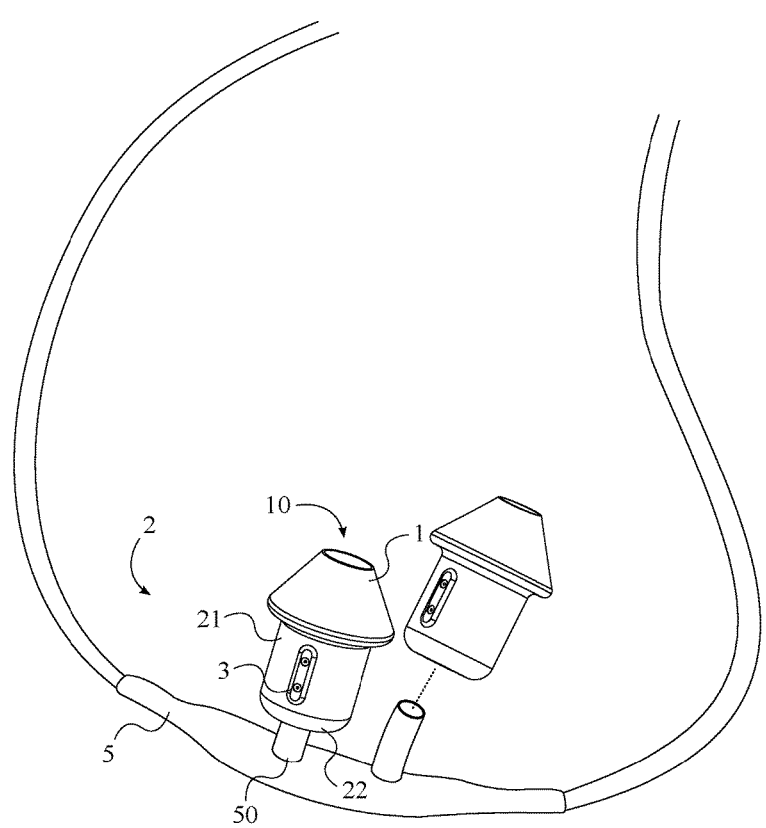
FIG. 13 is a perspective view, wherein the ergonomic nasal cannula is positioned overtop of the nasal prong.
Figure 14:
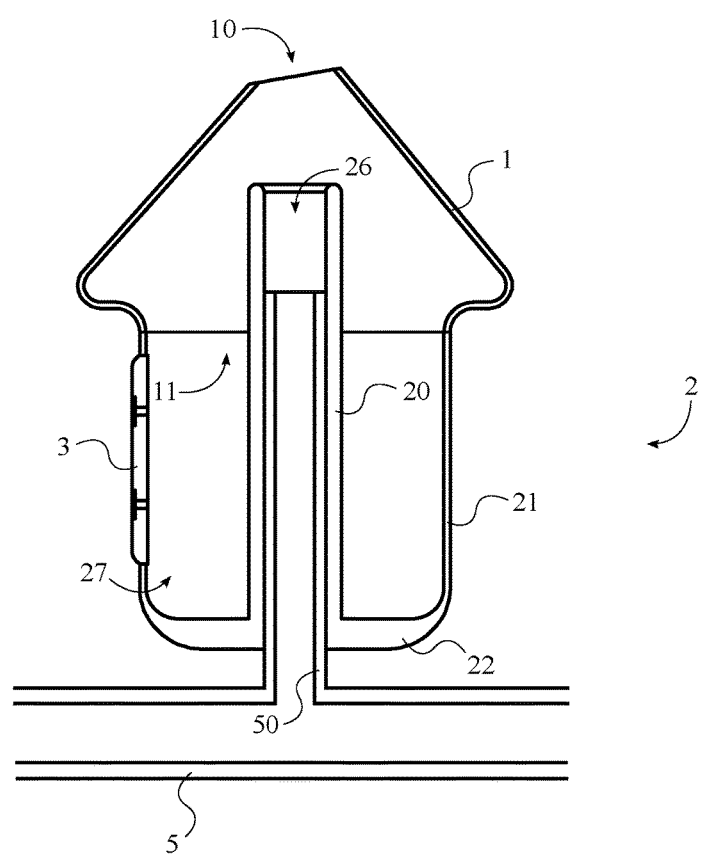
FIG. 14 is a right side sectional view, wherein the nasal prong is positioned into the primary airflow channel through the primary airflow opening.

In reference to FIG. 12-13, in the preferred embodiment of the present invention, the ergonomic nasal cannula is retrofit onto the nasal cannula tubing 5. The airflow structure 2 is adjacently attached to the nasal cannula tubing 5, such that the ergonomic nasal cannula is removable to be replaced or used with another tubing. In addition to channeling the flow of pure oxygen, the primary airflow opening 23 and the primary airflow channel 26 also provide a means for attaching the airflow structure 2 to a nasal prong 50 of the nasal cannula tubing 5. The primary airflow opening 23 is positioned about the bottom of the base plate 22, such that the airflow structure 2 is fitted over top of the nasal prong 50, as depicted through FIG. 12-13. As the airflow structure 2 is fitted over the nasal prong 50, the nasal prong 50 extends through the primary airflow opening 23, into the primary airflow channel 26, as depicted in FIG. 14. The primary airflow opening 23 and the primary airflow channel 26 are shaped and sized to form a snug fit around the nasal prong 50, creating a seal and securing the ergonomic nasal cannula in place.

Figure 15:
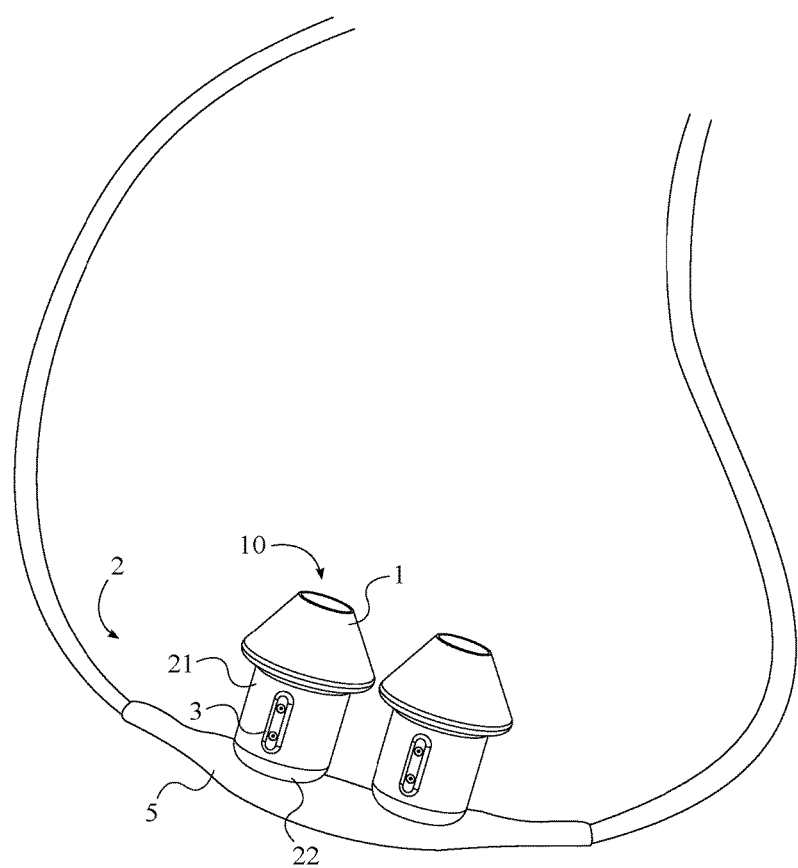
FIG. 15 is a perspective view, wherein the ergonomic nasal cannula is permanently connected to the nasal cannula tubing.

While the ergonomic nasal cannula is designed as a retrofit device in the preferred embodiment, the ergonomic nasal cannula can also be integrated directly into the nasal cannula tubing 5. In reference to FIG. 15, in such an embodiment, the airflow structure 2 is adjacently connected to the nasal cannula tubing 5, wherein the airflow structure 2 is fixed in place. As such, the ergonomic nasal cannula replaces the nasal prong 50 on the nasal cannula tubing 5. Under this configuration, users will not have to worry about the ergonomic nasal cannula inadvertently becoming detached from the nasal cannula tubing 5. However, it may be necessary to provide a way to remove the nasal cushion 1 from the airflow structure 2 in order to replace the nasal cushion 1, as the nasal cushion 1 may get worn down from continuous use. Additionally, the ability to switch out the nasal cushion 1 also provides a way for the user to adjust the size of the ergonomic nasal cannula without having to purchase a whole new tubing assembly. The nasal cushion 1 can be removably attached to the airflow structure 2 through a threaded connection, snap connection, or any other suitable means.

While the present invention has been discussed in regards to the delivery of oxygen through the airflow structure, it is to be understood that the present invention can be used in the delivery of any other number of gases to the airway of an individual, such as commonly used anesthetics.

Although the invention has been explained in relation to its preferred embodiment, it is to be understood that many other possible modifications and variations can be made without departing from the spirit and scope of the invention as hereinafter claimed.

What is claimed is:
1. An ergonomic nasal cannula comprises:
a nasal cushion comprising a nasal opening and a base opening;
an airflow structure comprising an inner lateral wall, an outer lateral wall, a base plate, a primary airflow opening, and a secondary airflow opening;
the primary airflow opening traversing through the base plate;
the inner lateral wall and the outer lateral wall being terminally connected to the base plate;
the inner lateral wall being perimetrically positioned about the primary airflow opening;
the inner lateral wall and the opening delineating a primary airflow channel;
the outer lateral wall being perimetrically positioned about the base plate;
the outer lateral wall and the inner lateral wall delineating a secondary airflow channel;
the secondary airflow opening traversing through the outer lateral wall;
the nasal cushion being perimetrically connected to the outer lateral wall opposite the base plate;
the base opening being positioned adjacent to the outer lateral wall;
the nasal opening being terminally positioned opposite the base opening;
a two-way valve; and
the two-way valve being mounted to the outer lateral wall, within the secondary airflow opening.

2. The ergonomic nasal cannula as claimed in claim 1 comprises:
the nasal cushion being impregnated with an anti-pathogenic material.

3. The ergonomic nasal cannula as claimed in claim 2, wherein the anti-pathogenic material is elemental silver.

4. The ergonomic nasal cannula as claimed in claim 1 comprises:
a nasal cannula tubing comprising a nasal prong;
the airflow structure being adjacently attached to the nasal cannula tubing; and
the nasal prong being positioned into the primary airflow channel through the primary airflow opening.

5. The ergonomic nasal cannula as claimed in claim 1 comprises:
a nasal cannula tubing; and
the airflow structure being adjacently connected to the nasal cannula tubing.

6. The ergonomic nasal cannula as claimed in claim 1 comprises:
the nasal cushion being removably attached to the outer lateral wall.

7. The ergonomic nasal cannula as claimed in claim 1 comprises:
the nasal cushion being tapered away from the airflow structure.

8. The ergonomic nasal cannula as claimed in claim 1 comprises:
the primary airflow opening being concentrically positioned with the base plate.

9. The ergonomic nasal cannula as claimed in claim 1 comprises:
the inner lateral wall traversing into the nasal cushion through the base opening.

10. The ergonomic nasal cannula as claimed in claim 1 comprises:
the airflow structure further comprises a tertiary airflow opening; and
the tertiary airflow opening traversing through the outer lateral wall.

11. The ergonomic nasal cannula as claimed in claim 10 comprises:
 a subsequent two-way valve; and
 the subsequent two-way valve being mounted to the outer lateral wall, within the tertiary airflow opening.

* * * * *